United States Patent
Cambronne (10) Patent No.: US 9,114,235 B2
(45) Date of Patent: Aug. 25, 2015

(54) THERAPEUTIC AGENT DELIVERY SYSTEM AND METHOD FOR LOCALIZED APPLICATION OF THERAPEUTIC SUBSTANCES TO A BIOLOGICAL LUMEN

(75) Inventor: Matthew David Cambronne, Stillwater, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 269 days.

(21) Appl. No.: 13/098,695

(22) Filed: May 2, 2011

(65) Prior Publication Data

US 2012/0109105 A1    May 3, 2012

Related U.S. Application Data

(60) Provisional application No. 61/330,617, filed on May 3, 2010.

(51) Int. Cl.
*A61M 31/00* (2006.01)
*A61M 25/10* (2013.01)
*A61L 29/16* (2006.01)
*A61M 25/06* (2006.01)

(52) U.S. Cl.
CPC ............... *A61M 25/10* (2013.01); *A61L 29/16* (2013.01); *A61L 2300/416* (2013.01); *A61M 2025/0681* (2013.01); *A61M 2025/105* (2013.01)

(58) Field of Classification Search
CPC ... A61F 2210/0004; A61F 2/18; A61L 27/14; A61L 27/56
USPC ......... 604/500–510, 514–520, 96.01–103.14, 604/104–109; 623/23.72, 1.38, 1.11
See application file for complete search history.

(56) References Cited

U.S. PATENT DOCUMENTS

| | | | |
|---|---|---|---|
| 4,665,918 A | 5/1987 | Garza et al. |
| 5,575,815 A | 11/1996 | Slepian et al. |
| 5,629,077 A | 5/1997 | Turnlund et al. |
| 5,674,287 A | 10/1997 | Slepian et al. |
| 5,749,922 A | 5/1998 | Slepian et al. |
| 5,766,584 A | 6/1998 | Edelman et al. |

(Continued)

FOREIGN PATENT DOCUMENTS

| | | |
|---|---|---|
| JP | H05509008 | 12/1993 |
| JP | H10502273 | 3/1998 |
| JP | 2005328893 | 12/2005 |

OTHER PUBLICATIONS

International Search Report from related PCT application No. PCT/US2011/034882 dated Jul. 18, 2011.

(Continued)

*Primary Examiner* — Phillip Gray
(74) *Attorney, Agent, or Firm* — Winthrop & Weinstine, P.A.

(57) ABSTRACT

The invention provides a system and method for localized application of therapeutic substances within a biological lumen and to the wall of the lumen. In various embodiments, a biodegradable tubular prosthesis comprising a plurality of pores is deployed within a biological lumen. Subsequent to, or in conjunction with, the deployment of the prosthesis, a drug-eluting balloon comprising at least one therapeutic agent is expanded within the lumen of the tubular prosthesis, thereby releasing the agent(s) from the balloon and delivering them to the prosthesis pores. The at least one therapeutic agent is then allowed to diffuse through the pores to the lumen wall.

25 Claims, 3 Drawing Sheets

(56) References Cited

U.S. PATENT DOCUMENTS

| | | | |
|---|---|---|---|
| 5,769,883 | A | 6/1998 | Buscemi et al. |
| 5,800,538 | A | 9/1998 | Slepian et al. |
| 5,947,977 | A | 9/1999 | Slepian et al. |
| 6,309,380 | B1 | 10/2001 | Larson et al. |
| 6,443,941 | B1 | 9/2002 | Slepian et al. |
| 6,605,115 | B1 | 8/2003 | Cooke et al. |
| 6,699,272 | B2 | 3/2004 | Slepian et al. |
| 7,044,965 | B1 | 5/2006 | Spielberg |
| 7,052,711 | B2 | 5/2006 | West et al. |
| 7,279,176 | B1 | 10/2007 | West et al. |
| 7,288,084 | B2 | 10/2007 | Li |
| 7,297,347 | B2 | 11/2007 | Domb |
| 7,806,925 | B2 | 10/2010 | Buscemi et al. |
| 2002/0165601 | A1 | 11/2002 | Clerc |
| 2005/0096731 | A1 | 5/2005 | Looi et al. |
| 2005/0271701 | A1 | 12/2005 | Cottone et al. |
| 2006/0266474 | A1 | 11/2006 | Burnside et al. |
| 2006/0271168 | A1* | 11/2006 | Kleine et al. .................. 623/1.38 |
| 2006/0287709 | A1 | 12/2006 | Rao |
| 2007/0055364 | A1 | 3/2007 | Hossainy et al. |
| 2007/0270940 | A1 | 11/2007 | Doty |
| 2008/0051881 | A1 | 2/2008 | Feng et al. |
| 2008/0097575 | A1 | 4/2008 | Cottone |
| 2008/0138378 | A1 | 6/2008 | Looi et al. |
| 2008/0311172 | A1 | 12/2008 | Schapira et al. |
| 2009/0069904 | A1* | 3/2009 | Picha .......................... 623/23.72 |
| 2010/0021519 | A1 | 1/2010 | Shenoy |
| 2010/0023108 | A1* | 1/2010 | Toner et al. .................. 623/1.11 |

OTHER PUBLICATIONS

A novel formulation for controlled release of heparin-DOCA conjugate dispersed as nanoparticles in polyurethane film, Moon et al., Nov. 29, 2000.

Polymeric endoluminal gel paving: hydrogel systems for local barrier creation and site-specific drug delivery, Slepian et al., Dec. 9, 1997.

Characterization of perivascular poly(lactic-co-glocolic acid) films containing paclitaxel, Jackson et al., Aug. 17, 2004.

Effect of plasticization on heparin release from biodegradable matrices, Vankatranam et al., Aug. 13, 2004.

Formulation and characterization of biodegradable nanoparticles for intravascular local drug delivery, Song et al., Oct. 28, 1997.

Perivascular delivery of heparin for the reduction of smooth muscle cell proliferation after endothelial injury, Teomim et al., Feb. 20, 2003.

Perivascular graft heparin delivery using biodegradable polymer wraps, Edelman et al., Sep. 13, 2000.

Biodegradable implant strategies for inhibition of restenosis, Orloff et al., Dec. 9, 1997.

Inhibition of postangioplasty restenosis using antisense approach, Vadim Tchaikovski, May 8, 2003.

* cited by examiner

THERAPEUTIC AGENT DELIVERY SYSTEM AND METHOD FOR LOCALIZED APPLICATION OF THERAPEUTIC SUBSTANCES TO A BIOLOGICAL LUMEN

CROSS-REFERENCE TO RELATED APPLICATIONS

The present application claims priority under 35 U.S.C. §119(e) to provisional application No. 61/330617, filed on May 3, 2010 entitled DEGRADEABLE DRUG DELIVERY DEVICE.

BACKGROUND OF THE INVENTION

1. Field of the Invention

The invention relates to systems, devices and methods for treating walls of biological lumens, e.g., animal lumens, with localized delivery of therapeutic agents.

2. Description of the Related Art

A variety of techniques and instruments have been developed for use in the removal or repair of tissue in biological conduits, e.g., without limitation, blood vessels and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes, leg pain and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patency of the opened artery. For non-calcified lesions, balloon angioplasty most often is used alone to open the artery, and stents often are placed to maintain patency of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patency of the artery.

Several kinds of rotational atherectomy devices have been developed for attempting to remove stenotic material. In one type of device, such as that shown in U.S. Pat. No. 4,990,134 (Auth), a burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently more than one size burr must be utilized to open an artery to the desired diameter.

U.S. Pat. No. 5,314,438 (Shturman) discloses another atherectomy device having a drive shaft with a section of the drive shaft having an enlarged diameter, at least a segment of this enlarged surface being covered with an abrasive material to define an abrasive segment of the drive shaft. When rotated at high speeds, the abrasive segment is capable of removing stenotic tissue from an artery. Though this atherectomy device possesses certain advantages over the Auth device due to its flexibility, it also is capable only of opening an artery to a diameter about equal to the diameter of the enlarged abrading surface of the drive shaft since the device is not eccentric in nature.

U.S. Pat. No. 6,494,890 (Shturman) discloses an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. Since the enlarged eccentric section comprises drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. In addition, some stenotic tissue may block the passageway so completely that the Shturman device cannot be placed therethrough. Since Shturman requires that the enlarged eccentric section of the drive shaft be placed within the stenotic tissue to achieve abrasion, it will be less effective in cases where the enlarged eccentric section is prevented from moving into the stenosis. The disclosure of U.S. Pat. No. 6,494,890 is hereby incorporated by reference in its entirety.

U.S. Pat No. 5,681,336 (Clement) provides an eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., 20,000-200,000 rpm. Essentially, the center of mass offset from the rotational axis of the drive shaft would result in development of significant centrifugal force, exerting too much pressure on the wall of the artery and creating too much heat and excessively large particles.

Another method of treatment of occluded vessels may include the use of stents. Stents may be placed at the site of a stenosis and expanded to widen the vessel, remaining in position as a vessel implant.

No matter the technique used to open an occluded conduit, e.g., blood vessel, and restore normal fluid flow therethrough, one problem remains: restenosis. A certain percentage of the treated conduits and vessels will reocclude (restenose) after a period of time; occurring in as many as 30-40% of the cases. When restenosis does occur, the original procedure may be repeated or an alternative method may be used to reestablish fluid, e.g., blood, flow.

The relevant commonality shared by each of the above treatment methods is that each one may result in some trauma to the conduit wall. Restenosis occurs for a variety of reasons;

each involving trauma. Small clots may form on the arterial wall. Small tears in the wall expose the blood to foreign material and proteins which are highly thrombogenic. Resulting clots may grow gradually and may even contain growth hormones released by platelets within the clot. Moreover, growth hormones released by other cells, e.g., macrophages, may cause smooth muscle cells and fibroblasts in the affected region to multiply in an abnormal fashion. There may be an injury in the conduit wall due to the above methods that results in inflammation which may result in the growth of new tissue.

It is known that certain therapeutic substances may have a positive effect on prevention and/or inhibition of restenosis. Several difficulties present themselves in the application of these substances to the affected region in a therapeutic dose. For example, the region in need of treatment is very small and localized. Fluid, e.g., blood, flow in the conduit is continuous, resulting in a flow boundary along the wall which must be disrupted so that the therapeutic substances may reach the localized region of interest within a dose range considered therapeutic. The art fails to adequately provide a mechanism for breaking through this flow boundary to target the region of interest; electing instead generally to place the therapeutic substance into the general flow of the conduit, either by intravenous means or intra-lumen infusion, at a dose that is much higher than therapeutic since the majority of the therapeutic substance will simply flow downstream and either be absorbed systemically or eliminated as waste. For example, intravenous medications are delivered systemically by vein, or regionally, e.g., through intra-lumen infusion without targeting the subject region. Such unnecessary systemic exposure results with unknown and unnecessary adverse results in regions, tissue, and/or organs that are distant from the region of interest. Clearly, systemic delivery and exposure is not well suited to treatment of diseases or conditions having a single intra-lumen region of interest.

The potential utility of localized application of a therapeutic dose of therapeutic substances is not limited to treatment of coronary arteries. Beyond coronary artery delivery, other sites of atherosclerosis, e.g., renal, iliac, femoral, distal leg and carotid arteries, as well as saphenous vein grafts, synthetic grafts and arterio-venous shunts used for hemodialysis would be appropriate biological conduits for a localized therapeutic substance delivery method and mechanism. Nor is the potential utility limited to blood vessels; any biological conduit having a region of interest amenable to treatment may benefit from such a treatment method and mechanism.

The present invention overcomes these deficiencies.

BRIEF SUMMARY OF THE INVENTION

The invention provides a system and method for localized application of therapeutic substances within a biological lumen and to the wall of the lumen. In various embodiments, a biodegradable tubular prosthesis comprising a plurality of pores is deployed within a biological lumen. Subsequent to, or in conjunction with, the deployment of the prosthesis, a drug-eluting balloon comprising at least one therapeutic agent is expanded within the lumen of the tubular prosthesis, thereby releasing the agent(s) from the balloon and delivering them to the prosthesis pores. The at least one therapeutic agent is then allowed to diffuse through the pores to the lumen wall.

The Figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

For the purposes of the present invention, the following terms and definitions apply:

"Bodily disorder" refers to any condition that adversely affects the function of the body.

The term "treatment" includes prevention, reduction, delay, stabilization, and/or elimination of a bodily disorder, e.g., a vascular disorder. In certain embodiments, treatment comprises repairing damage cause by the bodily, e.g., vascular, disorder and/or intervention of same, including but not limited to mechanical intervention.

A "therapeutic agent" comprises any substance capable of exerting an effect including, but not limited to therapeutic, prophylactic or diagnostic. Thus, therapeutic agents may comprise anti-inflammatories, anti-infectives, analgesics, anti-proliferatives, and the like including but not limited to antirestenosis drugs. Therapeutic agent further comprises mammalian stem cells. Therapeutic agent as used herein further includes other drugs, genetic materials and biological materials. The genetic materials mean DNA or RNA, including, without limitation, of DNA/RNA encoding a useful protein, intended to be inserted into a human body including viral vectors and non-viral vectors. Viral vectors include adenoviruses, gutted adenoviruses, adeno-associated virus, retroviruses, alpha virus, lentiviruses, herpes simplex virus, ex vivo modified cells (e.g., stem cells, fibroblasts, myoblasts, satellite cells, pericytes, cardiomyocytes, skeletal myocytes, macrophage), replication competent viruses, and hybrid vectors. Non-viral vectors include artificial chromosomes and mini-chromosomes, plasmid DNA vectors, cationic polymers, graft copolymers, neutral polymers PVP, SP1017, lipids or lipoplexes, nanoparticles and microparticles with and without targeting sequences such as the protein transduction domain (PTD). The biological materials include cells, yeasts, bacteria, proteins, peptides, cytokines and hormones. Examples for peptides and proteins include growth factors (FGF, FGF-1, FGF-2, VEGF, Endotherial Mitogenic Growth Factors, and epidermal growth factors, transforming growth factor .alpha.

and .beta., platelet derived endothelial growth factor, platelet derived growth factor, tumor necrosis factor .alpha., hepatocyte growth factor and insulin like growth factor), transcription factors, proteinkinases, CD inhibitors, thymidine kinase, and bone morphogenic proteins . These dimeric proteins can be provided as homodimers, heterodimers, or combinations thereof, alone or together with other molecules.

Therapeutic agents further includes cells that can be of human origin (autologous or allogeneic) or from an animal source (xenogeneic), genetically engineered, if desired, to deliver proteins of interest at the transplant site. Cells within the definition of therapeutic agents herein further include whole bone marrow, bone marrow derived mono-nuclear cells, progenitor cells (e.g., endothelial progenitor cells) stem cells (e.g., mesenchymal, hematopoietic, neuronal), pluripotent stem cells, fibroblasts, macrophage, and satellite cells.

Therapeutic agent also includes non-genetic substances, such as: anti-thrombogenic agents such as heparin, heparin derivatives, and urokinase; anti-proliferative agents such as enoxaprin, angiopeptin, or monoclonal antibodies capable of blocking smooth muscle cell proliferation, hirudin, and acetylsalicylic acid, amlodipine and doxazosin; anti-inflammatory agents such as glucocorticoids, betamethasone, dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives; anesthetic agents such as lidocaine, bupivacaine, and ropivacaine; anti-coagulants such as heparin, antithrombin compounds, platelet receptor antagonists, anti-thrombin anticodies, anti-platelet receptor antibodies, aspirin, dipyridamole, protamine, hirudin, prostaglandin inhibitors, platelet inhibitors and tick antiplatelet peptides; vascular cell growth promotors such as growth factors, Vascular Endothelial Growth Factors, growth factor receptors, transcriptional activators, and translational promotors; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms; anti-oxidants, such as probucol; antibiotic agents, such as penicillin, cefoxitin, oxacillin, tobranycin angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme, inhibitors including captopril and enalopril. The biologically active material can be used with (a) biologically non-active material(s) including a solvent, a carrier or an excipient, such as sucrose acetate isobutyrate, ethanol, n-methyl pymolidone, dimethyl sulfoxide, benzyl benxoate and benzyl acetate.

Further, "therapeutic agent" includes, in particular in a preferred therapeutic method of the present invention comprising the administration of at least one therapeutic agent to a procedurally traumatized, e.g., by an angioplasty or atherectomy procedure, mammalian vessel to inhibit restenosis. Preferably, the therapeutic agent is a cytoskeletal inhibitor or a smooth muscle inhibitor, including, for example, taxol and functional analogs, equivalents or derivatives thereof such as taxotere, paclitaxel, abraxane TM, coroxane TM or a cytochalasin, such as cytochalasin B, cytochalasin C, cytochalasin A, cytochalasin D, or analogs or derivatives thereof.

Additional specific examples of "therapeutic agents" that may be applied to a bodily lumen using various embodiments of the present invention comprise, without limitation:

L-Arginine;
Adipose Cells;
Genetically altered cells, e.g., seeding of autologous endothelial cells transfected with the beta-galactosidase gene upon an injured arterial surface;
Erythromycin;
Penicillin:
Heparin;
Aspirin;
Hydrocortisone;
Dexamethasone;
Forskolin;
GP IIb-IIIa inhibitors;
Cyclohexane;
Rho Kinsase Inhibitors;
Rapamycin;
Histamine;
Nitroglycerin;
Vitamin E;
Vitamin C;
Stem Cells;
Growth Hormones;
Hirudin;
Hirulog;
Argatroban;
Vapirprost;
Prostacyclin;
Dextran;
Erythropoietin;
Endothelial Growth Factor;
Epidermal Growth Factor;
Core Binding Factor A;
Vascular Endothelial Growth Factor;
Fibroblast Growth Factors;
Thrombin;
Thrombin inhibitor; and
Glucosamine, among many other therapeutic substances.

The therapeutic agent delivery system of the present invention can be used to apply the therapeutic agent to any wall surface of a biological lumen where a catheter can be inserted. Such biological lumen includes, inter alia, blood vessels, urinary tract, coronary vasculature, esophagus, trachea, colon, and biliary tract.

A therapeutically effective, or therapeutic, or effective, dose refers to that amount of therapeutic agent, which mitigates and/or provides therapy for the symptoms or condition. As the skilled artisan will readily recognize, therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. Pharmaceutical formulations which exhibit large therapeutic indices are preferred. The data obtained from cell culture assays and animal studies are used to formulate a range of dosage for human use. The dosage contained in such formulations is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical formulations may be administered every 3 to 4 days, every week, or biweekly depending on the half-life and clearance rate of the particular formulation. Normal dosage amounts may vary from about 0.1 µg to 100,000 µg, up to a total dose of about 1 g, or more in certain embodiments.

Moreover, the diffusive dose rate of the at least one therapeutic agent delivered and applied to the lumen wall may vary depending on the application and the size of the patient. An acceptable dose rate of the at least one therapeutic agent is within the range of about 0.01 mg/day to about 100 mg/day, more preferably about 0.2 mg/day to about 20 mg/day, still more preferably between 1 mg/day to about 5 mg/day.

In some embodiments, the formulation contains at least 1% by weight of the drug. For example, the formulation can contain at least 1%, at least 2%, at least 5%, at least 7%, at least 10%, at least 15%, at least 17%, at least 20%, at least 30%, at least 40%, at least 45% at least 50%, at least 60%, or at least 70%, e.g. 1-20%, 5-30%, 10-30%, 10-50%, 20-30% or 20-50% by weight of the drug. In other embodiments, the formulation can contain less than 1% of the drug.

Figure 1A:
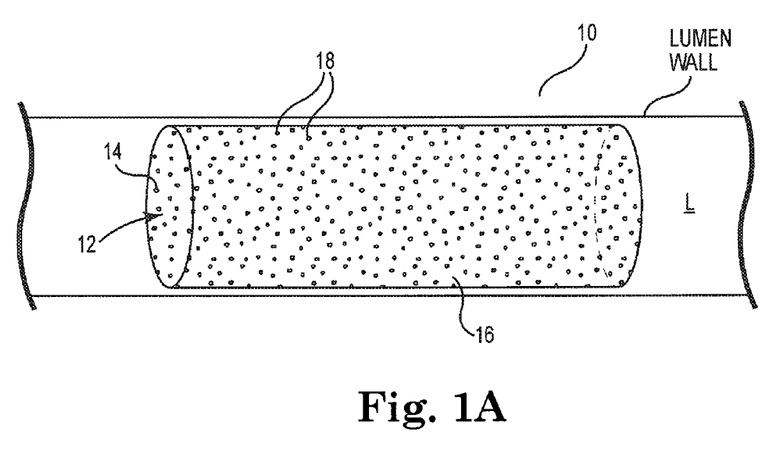
FIG. 1A is a side partial cutaway view of one embodiment of the present invention.
Figure 1B:
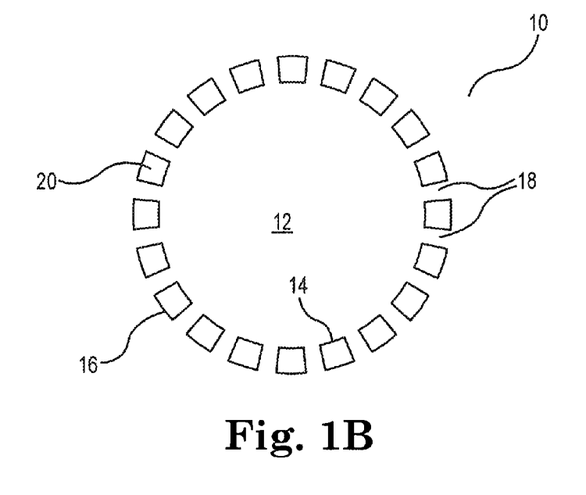
FIG. 1B is an end view one embodiment of the present invention.

Turning now to FIGS. 1A and 1B, the various embodiments of the present invention comprise a tubular therapeutic agent delivery prosthesis 10 comprising a cylindrical profile, a lumen 12 to allow biological fluid, e.g., blood, to flow therethrough, a cylindrical inner lumen surface 14, a cylindrical outer surface 16, a thin wall 20 defined by the cylindrical inner lumen surface 14 and cylindrical outer surface 16, and an open pore structure wherein a plurality of pores 18 allow fluid communication between the inner lumen surface 14 and the outer surface 16.

The tubular prosthesis may be comprised of at least one biodegradable material. Such material is known in the art. For example and without limitation, poly-L,D-lactic acid, poly-L-lactic acid, poly-D-lactic acid, polyglycolic acid, polylactic acid, polycaprolactone, polydioxanone, poly(lactic acid-ethylene oxide) copolymers, or combinations thereof may be suitable for the present invention. Further, Vainionp at al., Prog Polym. Sci., vol. 14, pp. 697-716 (1989); U.S. Pat. Nos. 4,700,704, 4,653,497, 4,649,921, 4,599,945, 4,532,928, 4,605,730, 4,441,496, and U.S. Pat. No. 4,435,590, all of which are incorporated herein by reference, disclose various compounds from which bioabsorbable stents can be fabricated. Materials may further include aliphatic polyesters, e.g., PLGA, PLAA, PLA, PDLLA, PDLA, PCL, PGA and PHB, polyanhydrides, aliphatic polycarbonates, POE, PDXO and the biodegradable polymer family known as polyketals. The material may, in addition to being biodegradable, also be bioabsorbable as is known in the art. Further, preferred time ranges for the degradation of the tubular prosthesis 10 when inserted in the biological lumen include a preferred range of about 1 week to about 6 months, a more preferred range of about 2 weeks to about 6 months, a most preferred range of about 2 weeks to about 4 months.

Pore 18 size is one of the factors to consider when controlling the release rate of the at least one therapeutic agent from the inserted prosthesis 10. A preferred pore size is within the range of 0.02 micron to 100 micron, a more preferred pore size is within the range of 5 micron to 100 micron. Larger pore sizes may be needed for larger molecules or stem cells.

Moreover, the pores 18 may comprise a gradient of diameter moving from the inner surface 14 to the outer surface 16. Depending upon the therapeutic agent(s) being used, the time frames involved and various other factors known to the skilled artisan, the pore gradient may comprise a smaller pore size at the inner surface 14 and a larger pore size at the outer surface 16, with a smooth gradual pore size increase moving from inner 14 to outer 16 surface. This arrangement will cause the therapeutic agent(s) to diffuse into the lumen wall more quickly. Alternatively, the pore gradient may comprise a larger pore size at the inner surface 14 and a smaller pore size at the outer surface 16, with a smooth gradual pore size decrease moving from inner 14 to outer 16 surface. This latter pore gradient configuration will slow the diffusion of the therapeutic agent(s) out of the pore 18 and into the lumen wall. The manufacturing process can, as the skilled artisan will readily recognize, be modified to accommodate the particular therapeutic agent(s) being delivered by the present invention.

Figure 2A:
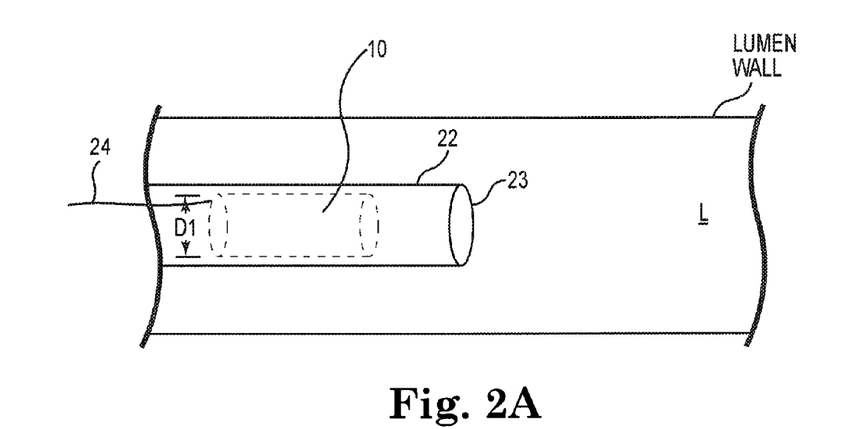
FIG. 2A is a side partial cutaway view of one embodiment of the present invention.
Figure 2B:
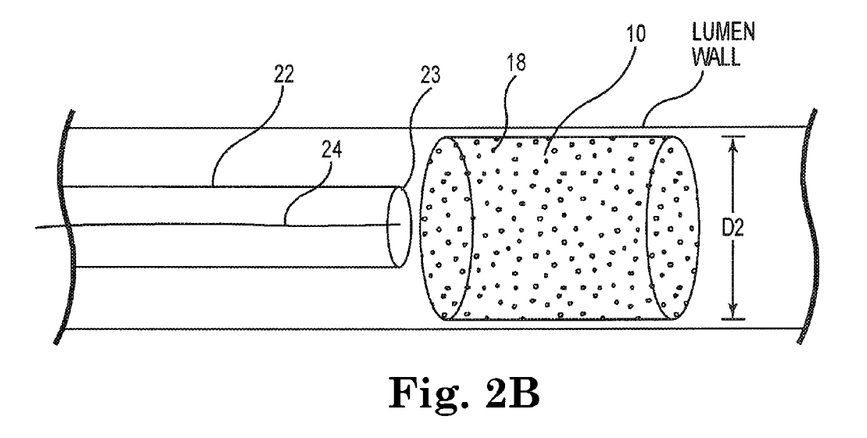
FIG. 2B is a side partial cutaway view of one embodiment of the present invention.

As illustrated in FIGS. 2A and 2B, the tubular prosthesis 10 of the present invention is in certain embodiments self-expanding. Thus, the material in these embodiments may allow deformation to a deformed configuration with a first diameter D1 and an expanded configuration with a second diameter D2, wherein the first diameter D1 is smaller than the second diameter D2. This allows delivery of the tubular prosthesis 10 through a delivery sheath or catheter 22 to the region of deployment within the patient's lumen L. Translating the tubular prostheses 10 in the deformed configuration through the delivery sheath or catheter 22 out of the distal end 23 of the sheath or catheter thus allows the tubular prosthesis 10 to realize the expanded configuration with the larger second diameter D2 as illustrated in FIG. 2B. Deployment of the tubular prosthesis 10 is complete when the self-expanding tubular structure 10, specifically the cylindrical outer surface 16 of the prosthesis 10, presses against the lumen wall.

Figure 3A:
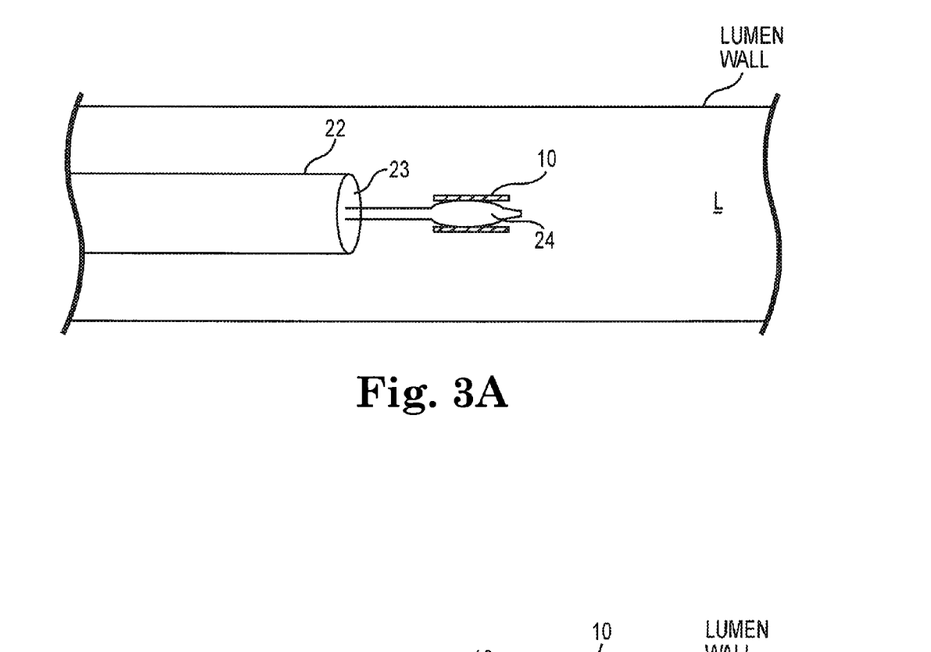
FIG. 3A is a side partial cutaway view of one embodiment of the present invention.
Figure 3B:
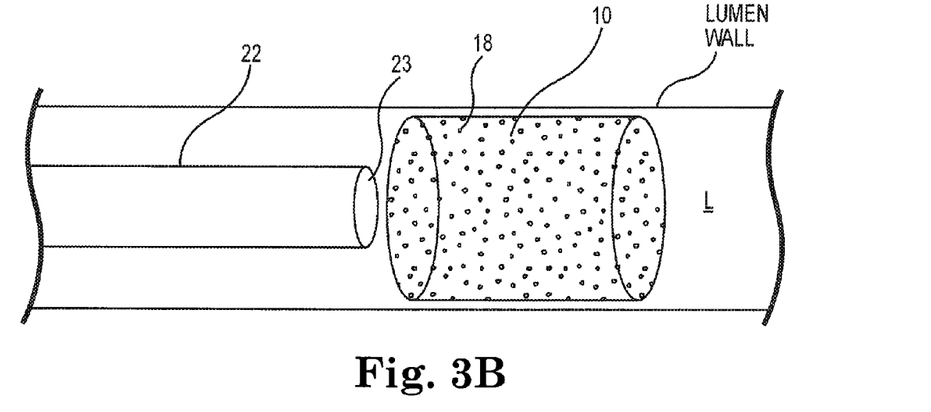
FIG. 3B is a side partial cutaway view of one embodiment of the present invention.

In other embodiments, illustrated in FIGS. 3A and 3B, the tubular prosthesis 10 of the present invention may be releasably adhered to the outer surface of an inflatable balloon 24 by which it is expanded for deployment within the lumen L and pressed against the lumen wall. Axially translating the balloon 24 and tubular prosthesis distally through, and ultimately out of the distal end 23 of the delivery sheath or catheter 22 allows the balloon 24 to be inflated by means well known in the art. In this manner, the outer surface 16 of the tubular prosthesis 10 is expanded to press against the wall of the lumen, thereby deploying the prosthesis 10. Deflation of the balloon 24 breaks the releasable adhesion of the tubular prosthesis 10 to the outer surface of the balloon 24, allowing the balloon 24 to be removed.

The present invention comprises deploying the tubular prosthesis within the lumen without preloading of any therapeutic agent in the pores 18. Nor does the tubular prosthesis material comprise any therapeutic agent therein whereby, as is known in the art, the agent is slowly released as the prosthetic material degrades. The present invention comprises introducing therapeutic agent(s) is introduced into the open cells, i.e., the pores 18, at the inner surface 14 of the tubular prosthesis 10 only after deployment in the lumen is complete, whereby the agent(s) slowly diffuse into the lumen wall through the pores 18 at the tubular prosthetic outer surface 16.

Introduction of the at least one therapeutic agent into the deployed tubular prosthesis may be achieved by a drug eluting balloon as is well known in the art. Thus, in certain embodiments the inflatable balloon 24 may serve two functions: expanding the tubular prosthesis 10 and deploying the prosthesis 10 within the lumen, and delivering therapeutic agent(s) from the drug eluting balloon 24 through pores 18 or the like as is well known in the art to the pores 18 of the tubular prosthesis 24. Delivery of the agent(s) from balloon 24 to the pores 18 of prosthesis 10 may be achieved in ways well known to the artisan skilled in drug eluting balloons, e.g., inflation of the balloon 24 may drive the agent(s) out of the balloon's reservoir. Alternative methods of delivering agent(s) to the balloon 24 for subsequent emission or elution therefrom and into the pores 18 of the prosthesis are disclosed in co-pending and commonly owned application Ser. No. 13/026,567 filed Feb. 14, 2011 and entitled "Devices and Methods for Low Shearing Local Delivery of Therapeutic Agents to the Wall of a Body Lumen", the entire contents of which are hereby incorporated by reference.

In the case where the tubular prosthesis 10 is self-expanding, i.e., moving from a first deformed configuration to a second expanded and deployed configuration, the inflatable balloon 24 may then be moved into the lumen 12 of the tubular prosthesis 10 and expanded, thereby releasing the therapeutic agent(s) contained in the drug eluting balloon 24 and delivering the agent(s) to the pores 18 of the tubular prosthesis 10.

The preferred material for the tubular prosthesis is, in certain embodiments, a biogradable open-celled foam. Various manufacturing methods for such material are known. For example, a composite of the biodegradable polymer and gelatin microspheres may be created. A thin walled tubular structure, i.e., the tubular prosthesis, may then be compression molded at a temperature greater than the glass transition point of the polymer. The gelatin may then be leached from the composite using DD water, thereby leaving an open-cell foam material with a pore size and morphology defined by the size of the gelatin spheres that were leached out of the composite. See U.S. Pat. No. 5,866,155 to Thompson, the entire contents of which are hereby incorporated by reference. Additional manufacturing methods for an open-celled material are disclosed in the following references, each of which is incorporated herein by reference: U.S. Pat. No. 5,699,175 to Mikos; 5,626,861 to Laurencin; 6,281,256 to Harris.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A system for inserting a cylindrical tubular prosthesis in a biological lumen and for delivering an effective dose of at least one therapeutic agent to the wall of the lumen, comprising:
    a cylindrical tubular prosthesis formed from a biodegradable material and comprising:
        a cylindrical wall defined by a cylindrical inner surface and a cylindrical outer surface,
        a lumen defined by the cylindrical wall,
        a plurality of pores, whereby the cylindrical inner surface and the cylindrical outer surface are in fluid communication,
        a smooth gradient of pore diameter within each of the plurality of pores between the cylindrical inner surface and the cylindrical outer surface, the gradient of diameter comprising a smaller pore size at the cylindrical inner surface and a larger pore size at the cylindrical outer surface with a smooth gradual pore size increase moving from the cylindrical inner surface to the cylindrical outer surface,
        a first deformed configuration having a first diameter, wherein the plurality of pores are open and without the at least one therapeutic agent therein,
        a second expanded configuration having a second diameter, wherein the second diameter is larger than the first diameter,
    a delivery sheath having a lumen therethrough, wherein the tubular prosthesis is axially translatable in the first deformed configuration, and a distal end, wherefrom the tubular prosthesis is released and expanded to the second expanded configuration and deployed against the lumen wall, and
    an inflatable drug-eluting balloon capable of axial translation into the lumen of the expanded deployed tubular prosthesis, the balloon comprising a reservoir therein, the reservoir containing an effective dose of at least one therapeutic agent therewithin for release into the plurality of pores, and further comprising an inflation means, whereby inflation of the balloon delivers the effective dose of the at least one therapeutic agent from the reservoir within the balloon to the plurality of pores, whereby the at least one therapeutic agent enters the gradient of pore diameter for diffusion therethrough at a rate controlled by the gradient of pore diameter to the lumen wall.

2. The system of claim 1, further comprising a wire in operative and releasable communication with the tubular prosthesis in the first deformed configuration, the wire arranged to translate the tubular prosthesis through the lumen of the delivery sheath and out of the distal end of the delivery sheath.

3. The system of claim 1, wherein the at least one therapeutic agent is selected from the group consisting of stem cells, anti-inflammatories, anti-infectives, analgesics, and anti-proliferatives.

4. The system of claim 1, wherein the at least one therapeutic agent comprises a cytoskeletal inhibitor and/or a smooth muscle inhibitor.

5. The system of claim 1, wherein the at least one therapeutic agent comprises taxol and functional analogs, equivalents and derivatives thereof.

6. The system of claim 1, wherein the effective dose is delivered to prevent restenosis following vascular trauma induced by atherectomy or angioplasty.

7. A method for delivering an effective dose of at least one therapeutic agent to a biological lumen wall, comprising:
    providing a cylindrical tubular prosthesis formed from a biodegradable material and comprising:
        a cylindrical wall defined by a cylindrical inner surface and a cylindrical outer surface;
        a lumen defined by the cylindrical wall;
        a plurality of pores, whereby the cylindrical inner surface and the cylindrical outer surface are in fluid communication and further comprising a gradient of pore diameter moving from the cylindrical inner surface to the cylindrical outer surface, wherein the plurality of pores are open and without the at least one therapeutic agent therein when the prosthesis is in a deformed configuration; and
        a smooth gradient of pore diameter within each of the plurality of pores between the cylindrical inner surface and the cylindrical outer surface;
    providing a delivery sheath having a lumen therethrough, wherein the cylindrical tubular prosthesis is axially translatable in a first deformed configuration, and a distal end, wherefrom the tubular prosthesis is released and expanded to a second expanded configuration and deployed against the lumen wall;

translating the tubular prosthesis axially and distally through the delivery sheath lumen in the first deformed configuration;

releasing the tubular prosthesis out of the distal end of the delivery sheath, thereby allowing the tubular prosthesis to achieve the second expanded configuration;

deploying the expanded tubular prosthesis in the lumen;

providing an inflatable drug-eluting balloon comprising an outer surface and capable of axial translation into the lumen of the expanded deployed cylindrical tubular prosthesis, the balloon comprising a reservoir therein, the reservoir containing the at least one therapeutic agent therewithin, and further comprising an inflation means;

translating the balloon into the lumen of the deployed tubular prosthesis;

inflating the balloon within the lumen of the deployed tubular prosthesis thereby expanding the tubular prosthesis to the second expanded configuration; and delivering the at least one therapeutic agent from the reservoir within the balloon to the plurality of pores, whereby the at least one therapeutic agent enters the gradient of pore diameter for diffusion therethrough at a rate controlled by the gradient of pore diameter to the lumen wall;

deflating the balloon; and allowing the tubular prosthesis to biodegrade.

8. The method of claim 7, further comprising selecting the at least one therapeutic agent from the group consisting of stem cells, anti-inflammatories, anti-infectives, analgesics, and anti-proliferatives.

9. The method of claim 7, further comprising ensuring that the at least one therapeutic agent comprises a cytoskeletal inhibitor and/or a smooth muscle inhibitor.

10. The method of claim 7, further comprising ensuring that the at least one therapeutic agent comprises taxol and functional analogs, equivalents and derivatives thereof.

11. The method of claim 7, further comprising delivering the effective dose to prevent restenosis following vascular trauma induced by atherectomy or angioplasty.

12. A method for delivering an effective dose of at least one therapeutic agent to a biological lumen wall, comprising:

providing a tubular prosthesis formed from a biodegradable material and comprising:
  a cylindrical wall defined by an inner surface and an outer surface;
  a lumen defined by the cylindrical wall;
  a deformed configuration having a first diameter and an expanded configuration having a second diameter, the second diameter being larger than the first diameter; and
  a plurality of pores, whereby the inner surface and the outer surface are in fluid communication and each of the plurality of pores comprises a gradient of pore diameter extending between the inner surface and the outer surface, wherein the plurality of pores are open and without the at least one therapeutic agent therein when the prosthesis is in the deformed configuration;

providing a delivery sheath comprising:
  a lumen therethrough, wherein the tubular prosthesis is axially translatable in the deformed configuration; and
  a distal end wherefrom the tubular prosthesis is released and deployed to the expanded configuration against the biological lumen wall;

providing an inflatable drug eluting balloon comprising an outer surface and capable of axial translation in the lumen of the expanded deployed tubular prosthesis, the balloon comprising a reservoir therein, the reservoir containing the at least one therapeutic agent therewithin, and further comprising an inflation means;

releasably attaching the inner surface of the tubular prosthesis in the deformed configuration to the outer surface of the inflatable drug eluting balloon;

translating the inflatable drug eluting balloon with the tubular prosthesis in the deformed configuration releasably attached thereto axially and distally through the delivery sheath lumen;

releasing the inflatable drug eluting balloon with the releasably attached tubular prosthesis out of the distal end of the delivery sheath;

inflating the balloon, whereby the tubular prosthesis achieves the expanded configuration;

deploying the expanded tubular prosthesis against the biological lumen wall;

releasing the effective dose of the at least one therapeutic agent from the reservoir in the balloon;

delivering the released effective dose of the at least one therapeutic agent to the plurality of pores;

deflating the balloon;

allowing the released effective dose of the at least one therapeutic agent to diffuse through the plurality of pores to the biological lumen wall; and allowing the tubular prosthesis to biodegrade.

13. The method of claim 12, further comprising selecting the at least one therapeutic agent from the group consisting of stem cells, anti-inflammatories, anti-infectives, analgesics, and anti-proliferatives.

14. The method of claim 12, further comprising ensuring that the at least one therapeutic agent comprises a cytoskeletal inhibitor and/or a smooth muscle inhibitor.

15. The method of claim 12, further comprising ensuring that the at least one therapeutic agent comprises taxol and functional analogs, equivalents and derivatives thereof.

16. The method of claim 12, further comprising delivering the effective dose to prevent restenosis following vascular trauma induced by atherectomy or angioplasty.

17. A system for inserting a cylindrical tubular prosthesis in a biological lumen and for delivering an effective dose of at least one therapeutic agent to the wall of the lumen, comprising:

a cylindrical tubular prosthesis formed from a biodegradable material and comprising:
  a cylindrical wall defined by a cylindrical inner surface and a cylindrical outer surface,
  a lumen defined by the cylindrical wall,
  a plurality of pores, whereby the cylindrical inner surface and the cylindrical outer surface are in fluid communication,
  a smooth gradient of pore diameter within each of the plurality of pores between the cylindrical inner surface and the cylindrical outer surface, the gradient of diameter comprising a larger pore size at the cylindrical inner surface and a smaller pore size at the cylindrical outer surface with a smooth gradual pore size decrease moving from the cylindrical inner surface to the cylindrical outer surface, a first deformed configuration having a first diameter, wherein the plurality of pores are open and without the at least one therapeutic agent therein, a second expanded configuration having a second diameter, wherein the second diameter is larger than the first diameter, a delivery sheath having a lumen therethrough, wherein the tubular prosthesis is axially translatable in the first deformed configuration, and a distal end, wherefrom the tubular prosthesis is released and expanded to the second expanded configuration and deployed against the lumen wall, and an inflatable drug-eluting balloon capable of axial translation into the lumen of the expanded deployed tubular prosthesis, the balloon comprising a reservoir therein, the reservoir containing an effective dose of at least one therapeutic agent therewithin for release into the plurality of pores, and further comprising an inflation means, whereby inflation of the balloon delivers the effective dose of the at least one therapeutic agent from the reservoir within the balloon to the plurality of pores, whereby the at least one therapeutic agent enters the gradient of pore diameter for diffusion therethrough at a rate controlled by the gradient of pore diameter to the lumen wall.

18. A system for inserting a cylindrical tubular prosthesis in a biological lumen and for delivering an effective dose of at least one therapeutic agent to the wall of the lumen, comprising:

a delivery sheath having a lumen therethrough, wherein the cylindrical tubular prosthesis is axially translatable in a first deformed configuration, and a distal end, wherefrom the tubular prosthesis is released and expanded to a second expanded configuration and deployed against the lumen wall;

a cylindrical tubular prosthesis formed from a biodegradable material and comprising:

a cylindrical wall defined by a cylindrical inner surface and a cylindrical outer surface, a lumen defined by the cylindrical wall, a plurality of pores, whereby the cylindrical inner surface and the cylindrical outer surface are in fluid communication and further comprising a gradient of pore diameter moving from the cylindrical inner surface to the cylindrical outer surface, wherein the plurality of pores are open and without the at least one therapeutic agent therein when the prosthesis is in a deformed configuration, and a smooth gradient of pore diameter within each of the plurality of pores between the cylindrical inner surface and the cylindrical outer surface, and an inflatable drug-eluting balloon having an outer surface and capable of axial translation into the lumen of the expanded deployed cylindrical tubular prosthesis, the balloon comprising a reservoir therein, the reservoir containing at least one therapeutic agent therewithin, and further comprising an inflation means, whereby inflation of the balloon expands the tubular prosthesis to the second expanded configuration and delivers the at least one therapeutic agent from the reservoir within the balloon to the plurality of pores, whereby the at least one therapeutic agent enters the gradient of pore diameter for diffusion therethrough at a rate controlled by the gradient of pore diameter to the lumen wall.

19. The system of claim 18, wherein the gradient of pore size diameter comprises pores with a smaller pore size at the cylindrical inner surface and a larger pore size at the cylindrical outer surface with a smooth gradual pore size increase moving from the cylindrical inner surface to the cylindrical outer surface.

20. The system of claim 19, further comprising the gradient of pore size diameter comprising pores with a larger pore size at the cylindrical inner surface and a smaller pore size at the cylindrical outer surface with a smooth gradual pore size decrease moving from the cylindrical inner surface to the cylindrical outer surface.

21. The system of claim 1, wherein the reservoir within the balloon is pre-loaded with the at least one therapeutic agent.

22. The system of claim 1, comprising a therapeutic agent delivery system for delivering the at least one therapeutic agent into the reservoir within the balloon.

23. The system of claim 17, comprising a therapeutic agent delivery system for delivering the at least one therapeutic agent into the reservoir within the balloon.

24. The system of claim 18, wherein the reservoir within the balloon is pre-loaded with the at least one therapeutic agent.

25. The system of claim 18, comprising a therapeutic agent delivery system for delivering the at least one therapeutic agent into the reservoir within the balloon.

* * * * *